United States Patent [19]

Greiner et al.

[11] Patent Number: 5,246,954
[45] Date of Patent: Sep. 21, 1993

[54] PROCESS FOR FOLIAR FUNGICIDE TREATMENT AND FUNGICIDE COMPOSITION FOR IMPLEMENTING THE PROCESS

[75] Inventors: Alfred Greiner, St Cyr Au Mont D'Or; Jean Hutt, Lyon; Jacques Mugnier, La Balme, De Sillingy; Regis Pepin, Rilleux La Pape, all of France

[73] Assignee: Rhone-Poulenc Secteur Agrochimie, Lyon, France

[21] Appl. No.: 714,725

[22] Filed: Jun. 13, 1991

[30] Foreign Application Priority Data

Jun. 13, 1990 [FR] France ................................ 9007606

[51] Int. Cl.⁵ ...................... A01N 43/64; A01N 47/10
[52] U.S. Cl. .................................. 514/383; 514/476; 514/491
[58] Field of Search ...................... 514/383, 476, 491

[56] References Cited

FOREIGN PATENT DOCUMENTS 378953  7/1990  European Pat. Off. .

OTHER PUBLICATIONS

Worthing et al., The Pesticide Manual, 8th ed., pp. 510–513, 848 and 849.
Jeann et al., C.A., vol. 114 (1991) 114:81835y.

Primary Examiner—Allen J. Robinson
Attorney, Agent, or Firm—Morgan & Finnegan

[57] ABSTRACT

The present invention relates to a process for the control of fungal disease of plants by applying to the leaves of the plants:
  a)  2-(4-chlorobenzylidene)-5,5-diemethyl-1-(1H-1,2,4-triazol-1-ylmethyl)-1-cyclopentanol;
  b)  one or more fungicides suitable for protecting against the said fungal diseases and to compositions which may be used in the process.

20 Claims, No Drawings

PROCESS FOR FOLIAR FUNGICIDE TREATMENT AND FUNGICIDE COMPOSITION FOR IMPLEMENTING THE PROCESS

The present invention relates to a fungicidal composition intended in particular, for the protection of cultivated plants, comprising (a) 2-(4-chlorobenzylidene)-5,5-dimethyl-1-(1H-1,2,4-triazol-1-ylmethyl)-1-cyclopentanol, (b) one or more fungicides, (c) an agriculturally acceptable inert carrier and (d) optionally an agriculturally acceptable surface-active agent.

The invention also relates to a process for protecting plants, by curative or prophylactic means, against fungal diseases by applying an effective dose of a composition according to the invention or of the individual active components (a) and (b) to the leaves of the plants.

2-(4-Chlorobenzylidene)-5,5-dimethyl-1-(1H-1,2,4-triazol-1-ylmethyl)-1-cyclopentanol is described in European Patent Application No. 89/420,520 filed on 27th Dec. 1989 and unpublished to date.

The compound 2-(4-chlorobenzylidene)-5,5-dimethyl-1-(1H-1,2,4-triazol-1-ylmethyl)-1-cyclopentanol may be prepared in the following manner:

100 ml of a 10% aqueous solution of sodium hydroxide were added to a mixture of 10 g of 2,2-dimethylcyclopentanone and 13.8 g of 4-chlorobenzaldehyde in 100 ml of ethanol at 0° C. After 30 minutes, a thick slurry was filtered off and the solid washed and then dried. 12.5 g of 2,2-dimethyl-5-(4-chlorobenzylidene)-1-cyclopentanone with a melting point of 120° C. were obtained. This compound, dissolved in 50 ml of THF, was added to a solution formed in the following manner: 1.9 g of sodium hydride (80% dispersion in mineral oil) in 50 ml of anhydrous DMSO were heated to 80° C. until complete dissolution of the solid. The solution was then diluted with 100 ml of THF, then cooled to −10° C. A solution of 11.5 g of trimethylsulphonium iodide in 80 ml of dimethyl sulphoxide were added to the mixture in the course of ten minutes and the mixture was stirred for 15 minutes at −10° C. A solution of 11.8 g of 2,2-dimethyl-4-chloro-5-(4-chlorobenzylidene)-1-cyclopentanone was then added in 100 ml of THF.

The mixture thus obtained was left at room temperature then poured into water and extracted with ether, washed with water, dried and distilled. 7-(4-Chlorobenzylidene)-4,4-dimethyl-1-oxaspiro[2.4]heptane, which was directly used in the subsequent stage, was obtained.

A mixture of 5 g of product with 2.8 g of 1,2,4-triazole and 11 g of potassium carbonate was heated in 40 ml of N,N-dimethylformamide for 4 hours. The mixture was poured into water and extracted with ethyl acetate. The organic phase was washed, dried and recrystallized to yield the stated product having a melting point of 143° C.

The chemical structure of 2-(4-chlorobenzylidene)-5,5-dimethyl-1-(1H-1,2,4-triazol-1-ylmethyl)-1-cyclopentanol obtained is given below.

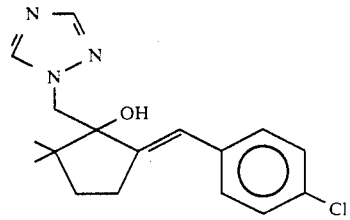

The structure of the compound is, in a very large majority of cases (>95%), that in which the para-chlorophenyl group is in the E position with respect to the carbon bearing the hydroxide group.

2,2-Dimethylcyclopentanone may be obtained in a manner which is known in the literature or is available commercially (see Fine Chemical Directory).

When choosing the fungicides of component (b) suitable for the protection of plants, those skilled in the art may usefully refer to the information given in reference works which state the absence of phytotoxicity for the said products as well as their efficacy against any particular disease.

These works include the "Index phytosanitaire" [Index of plant-protection agents], 1990 Edition, ACTA, 75595 PARIS CEDEX 12.

The fungicide compositions according to the invention typically contain 0.5 to 95% by weight of active material. As described herein, unless otherwise specified, percentages are by weight.

The term "carrier", in the present text, designates an organic or inorganic material, natural or synthetic, with which the active material is combined in order to facilitate its application to the plant, seeds or soil. This carrier is therefore generally inert and must be agriculturally acceptable, particularly on the treated plant. The carrier may be solid (clays, natural or synthetic silicates, silica, resins, waxes, solid fertilizers, and the like) or liquid (water, alcohols, ketones, petroleum fractions, aromatic or paraffinic hydrocarbons, chlorinated hydrocarbons, liquefied gases, and the like).

The surface-active agent may be an emulsifying, dispersing or wetting agent of the ionic or nonionic type. The following may be mentioned by way of example: polyacrylic acid salts, lignosulphonic acid salts, phenolsulphonic or naphthalenesulphonic acid salts, polycondensates of ethylene oxide and fatty alcohols or fatty acids or fatty amines, substituted phenols (alkylphenols or arylphenols in particular), ester salts of sulphosuccinic acids, taurine derivatives (alkyltaurates in particular), phosphoric esters of alcohols or of polyoxyethylated phenols. The presence of at least one surface-active agent is essential given that the active material and/or the inert carrier are insoluble in water and that the vector agent of the application is water.

These compositions may also contain other ingredients such as, for example, protective colloids, adhesives, thickeners, thixotropic agents, penetrating agents, stabilizers, sequestrants, pigments, colorants and polymers.

More generally, the compositions according to the invention may be combined with all those solid or liquid additives found in the usual formulation procedures.

Among the compositions, solid or liquid compositions may generally be mentioned.

By way of solid composition forms, the following are included: powders for dusting or dispersing (with a content of active material (i.e. fungicide (a) and one or more (b) fungicides) which may be as high as 100%) and granules, particularly those obtained by extrusion, by compaction, by impregnation of a granulated carrier and by granulation from a powder (the content of active material in these granules being between 1 and 80% in the latter cases).

The compositions may furthermore be used in the form of a powder for dusting; a composition comprising 50 g of active material, 10 g of finely divided silica and 970 g of talc may also be used; these constituents are mixed and ground and the mixture is applied by dusting.

By way of liquid composition forms or forms intended to constitute liquid compositions on application, the following are included: solutions, in particular water-soluble concentrates, emulsifiable concentrates, emulsions, concentrated suspensions, aerosols, wettable powders (or spray powder) and pastes.

The emulsifiable or soluble concentrates generally comprise 10 to 80% of active material; the emulsions or solutions ready for application contain, for their part, 0.01 to 20% of active material.

For example, in addition to the solvent, the emulsifiable concentrates may contain when necessary, 2 to 20% of appropriate additives such as the stabilizers, surface-active agents, penetrating agents, corrosion inhibitors, colorants or adhesives previously mentioned.

From these concentrates, emulsions of any desired concentration, which are particularly suitable for application to leaves, may be obtained by dilution with water.

The concentrated suspensions, which can also be applied by spraying, are prepared so as to obtain a stable fluid product which does not form deposits, and they normally contain from 10 to 75% of active material, 0.5 to 15% of surface-active agents, 0.1 to 10% of thixotropic agents, 0 to 10% of appropriate additives, such as pigments, colorants, antifoams, corrosion inhibitors, stabilizers, penetrating agents and adhesives and, by way of carrier, water or an organic liquid in which the active material is barely soluble or insoluble: some organic solid materials or inorganic salts may be dissolved in the carrier to help prevent sedimentation or as antifreeze for water.

The wettable powders (or spray powders) are normally prepared so that they contain 20 to 95% of active material, and they normally contain, in addition to the solid carrier, from 0 to 5% of a wetting agent, 3 to 10% of a dispersing agent and, when necessary, from 0 to 10% of one or more stabilizers and/or other additives, such as pigments, colorants, penetrating agents, adhesives, or anticoagulating agents, and the like.

To obtain these spray powders or wettable powders, the active materials are thoroughly mixed in appropriate mixers with the additional substances and they are ground using mills or other appropriate grinders. Spray powders are thereby obtained having wettability and ability to form suspensions which are advantageous; they can be suspended in water at any desired concentration and these suspensions may be used very advantageously, in particular for application to plant leaves.

In place of the wettable powders, pastes may be prepared. The conditions and methods for the preparation and the use of these pastes are similar to those for wettable powders or spray powders.

The dispersible granules are normally prepared by agglomeration, in appropriate granulation systems, of the composition of the wettable powder type.

As already indicated, the dispersions and aqueous emulsions, for example, the compositions obtained by diluting a wettable powder or an emulsifiable concentrate according to the invention with water, are included within the general scope of the present invention. The emulsions may be of the water-in-oil or oil-in-water types and they may have a thick consistency like that of a "mayonnaise".

Among these compositions, those persons skilled in the art will advantageously choose that or those which is/are suitable in relation to the combinations chosen.

The compositions according to the invention may be used in a preventive or curative capacity for combating fungi, particularly of the basidiomycete, ascomycete, adelomycete or imperfect fungi types, in particular rusts, oidium, eyespot, fusarioses, *Fusarium roseum, Fusarium nivale,* net blotch, leaf blotch, septoria spot, bunt, rhizoctonioses of vegetables and plants in general and, in particular, of cereals such as wheat, barley, rye, oats and their hybrids and also rice and maize.

The compositions according to the invention are active in particular against fungi particularly of the following types: basidiomycetes, ascomycetes, adelomycetes or imperfect fungi such as *Botrytis cinerea, Erysiphe graminis, Puccinia recondita, Piricularia oryzae, Cercospora beticola, Puccinia striiformis, Erysiphe cichoracearum, Fusarium oxysporum (melonis,* for example), *Pyrenophora avenae, Septoria tritici, Venturia inaequalis, Whetzelinia sclerotiorum, Monilia laxa, Mycosphaerella fijiensis, Marssonina panettoniana, Alternaria solani, Aspergillus niger, Cercospora arachidicola, Cladosporium herbarum, Helminthosporium oryzae, Penicillium expansum, Pestalozzia sp, Phialophora cinerescens, Phoma betae, Phoma foveata, Phoma lingam, Ustilago maydis, Verticillium dahliae, Ascochyta pisi, Guignardia bidwellii, Corticium rolfsii, Phomopsis viticola, Sclerotinia sclerotiorum, Sclerotinia minor, Coryneum cardinale, Rhizoctonia solani.*

They are also and furthermore active against the following fungi: *Acrostalagmus koningi, Alternaria, Colletotrichum, Diplodia natalensis, Gaeumannomyces graminis, Gibberella fujikuroi, Hormodendron cladosporioides, Lentinus degener* or *tigrinus, Lenzites quercina, Memnoniella echinata, Myrothecium verrucaria, Paecylomyces varioti, Pellicularia sasakii, Phellinus megaloporus, Polystictus sanguineus, Poria vaporaria, Sclerotium rolfsii, Stachybotris atra, Stereum, Stilbum sp., Trametes trabea, Trichoderma pseudokoningi, Trichothecium roseum.*

The compositions of the invention are particularly useful due to their wide spectrum in relation to cereal diseases (oidium, rust, eyespot, leaf blotch, net blotch, septoria spot and fusarioses). They are also of great interest because of their activity on grey mould (Botrytis) and leaf spot, and as a result, they can be applied to products of crop propagation as varied as vines, market garden crops, arboricultural crops and tropical crops such as groundnuts, banana plants, coffee plants, pecan nuts and the like.

In addition to the applications already described above, the compositions according to the invention further possess an excellent biocidal activity towards numerous other varieties of microorganisms amongst which there may be mentioned, without implying a limitation, fungi such as those of the genera:

Pullularia, such as the *P. pullulans* species,
Chaetonium, such as the *C. globosum* species,
Aspergillus, such as the *Aspergillus niger* species,
Coniophora, such as the *C. puteana* species.

Because of their biocidal activity, the compositions of the invention make it possible to effectively combat microorganisms whose proliferation creates numerous problems in the agricultural and industrial sectors. To that effect, they are particularly well suited to the protection of plants or industrial products such as timber, leather, paints, paper, rope, plastics and industrial water systems.

They are more particularly well suited to the protection of lignocellulose products and of timber in particular, whether this be timber for furniture or for building, or timber exposed to adverse weather conditions such as fencing timber, vine posts and railway sleepers.

The compositions according to the invention are generally employed with organic solvents and may optionally be combined with one or more known biocidal products such as pentachlorophenol, metal salts particularly of copper, manganese, cobalt, chromium and zinc derived from inorganic or carboxylic acids (heptanoic, octanoic and naphthenic acids); tin organic complexes, mercaptobenzothiazole, or insecticides such as pyrethroids or organochlorides.

The compositions may most often contain one fungicide of component (b) (binary combination) or two (ternary combination) or even four (quaternary combination).

The fungicides which are suitable within the scope of the present invention are advantageously chosen from among the following subclasses:

1. chlorinated or nitrated benzene derivatives such as quintozene or chlorothalonil,
2. dicarboximide derivatives such as captan, folpel, captafol, iprodione, procymidone and vinclozolin,
3. derivatives comprising one or more heterocyclic compounds such as quinolines (ethoxyquin), morpholines (dodemorph, tridemorph, fenpropimorph, 4-[3-(4-chlorophenyl)-2-methylpropyl]-2,6-dimethylmorpholine described in EP-A-262870), pyrroles such as fenpiclonil or 4-(2,3-dichlorophenyl)pyrrole-3-carbonitrile and piperidines (fenpropidin),
4. phosphorous acid derivatives such as metal phosphites such as phosetyl-A1 and phosphorous acid itself and its calcium or potassium salts,
5. dithiocarbamic acid derivatives such as maneb, mancozeb or zineb,
6. phenol derivatives such as dinocap or binapacryl,
7. quinone derivatives such as dithianon, chloranil, triazoxide,
8. carbamic acid and benzimidazole derivatives such as carbendazim, benomyl, thiophanate-methyl or dithiocarbamates such as thiram,
9. sulphur-containing derivatives such as dazomet or etridiazole or sulphur,
10. amines and amides such as dichloran, carboxin, triflorin, cymoxanil, metalaxyl, ofurace, oxadixyl, ampropylfos,
11. diazines such as chinomethionat, fenarimol, anilazine, nuarimol, bupirimate, ethyrimol, pyrazophos,
12. sulphamides such as dichlofluanid, tolyfluanid,
13 guanidines such as doguadine, guazatine triacette, iminoctadine dodecylbenzenesulphonate,
14. triazoles such as, for example, those described in the British Patent No. 2046260 whose content is incorporated by reference such as dinizconazole or other known triazoles, propiconazole, triadimefon, triadimenol, dichlobutrazol, bitertanol, penconazol, flutriafol, tebuconazol, flusilazole,
15. imidazoles such as prochloraz or imazalil,
16. copper or organic or inorganic copper derivatives such as oxine-copper.

The common names of these compounds are approved by the British Standards Institution and correspond to the active materials described in The Pesticide Manual, 8th edition, 1987.

Preferably, the weight ratio of the compound of component a) to the fungicides of component (b) described above is between 0.0003 and 3,000 and advantageously between 0.001 and 1,000.

The following fungicides of component (b) are preferred:
maneb,
fenpropimorph,
thiram,
iprodione,
phosethyl-Al,
ethyrimol.

The invention also provides a method for the control of fungal disease of a plant suffering from, or subject to, fungal disease, which comprises applying to the leaves of the plant (a) 2-(4-chlorobenzylidene)-5,5-dimethyl-1-(1H-1,2,4-triazol-1-ylmethyl)-1-cyclopentanol and (b) one or more other fungicides effective against the fungal disease. It will be understood that the amount of active material should be effective to combat fungal growth and be non-phytotoxic.

These compositions can be advantageously applied in doses of 0.002 to 1 kg/ha and more specifically of 10 to 600 g/ha.

Among crops, the following may be mentioned: cereals (wheat or barley, for example), vines, market, garden crops, rice, maize, arboricultural crops, tropical crops, beet and rape.

The process may be implemented by using a composition which is ready for use, or by mixing various active materials immediately before use (tank mix). The composition may also be formed in situ by successive applications to the leaf of the various active materials.

The invention is further illustrated by the examples given below, which are not intended to limit the invention.

EXAMPLE 1

In vivo test on "Puccinia recondita", causative agent of brown rust in wheat

An aqueous emulsion of active material (fungicide (a) and maneb mixture) having the following composition:
test active material: 90 mg,
Tween 80 (surface-active agent composed of a sorbitan polyoxyethylene-derivative oleate) diluted to 10% in water: 0.45 ml,
water: 90 ml
is prepared by grinding the components finely.

This aqueous emulsion is then diluted with water to obtain the desired concentration.

Wheat, sown in pots of loam, is treated at the stage when it is 10 cm high by spraying with aqueous emulsions (called sprays) of the same composition as that described above and at various concentrations of the test compound. The trial is repeated twice for each concentration.

After 24 hours, an aqueous suspension of spores (50,000 sp/cm$^3$) is sprayed onto the wheat; this suspension was obtained from contaminated plants. The wheat is then placed for 48 hours in an incubation cell at about 18° C. and about 100% relative humidity.

After these two days, the relative humidity is brought to 60%. The condition of the plants is monitored between the 11th and 15th day after the contamination by comparison with the untreated control.

Under these conditions, the following results are observed:

| Fungicide (a) | Per cent efficacy mg/1 MANEB | | | | | |
|---|---|---|---|---|---|---|
| | 0 | 4 | 12 | 37 | 111 | 333 |
| 0 | 0 | 27.5 | 32.5 | 72.5 | 95 | 97.25 |
| 4 | 0 | 18.75 | 40 | 52.5 | 76.25 | 95.25 |
| 12 | 36.25 | 36.25 | 42.5 | 62.5 | 81.25 | 98 |
| 37 | 57.5 | 65 | 75 | 85 | 92.5 | 98.5 |
| 111 | 80 | 80 | 81.25 | 85 | 90 | 98.5 |
| 333 | 95.7 | 98 | 97.75 | 98.25 | 98.75 | 100 |

EXAMPLE 2

In vivo test on "*Erysiphe graminis*" f.sp. hordei responsible for oidium in barley A combination of the (a) fungicide and fenpropimorph is prepared according to the preceding method.

Barley, sown in pots of loam, is treated at the stage when it is 10 cm high by spraying with an aqueous emulsion (called spray) at the concentration indicated hereafter. The trial is repeated twice. After 24 hours, the barley plants are dusted with *Erysiphe graminis* spores, the dusting being carried out using diseased plants.

Readings are made 8 to 12 days after the contamination.

Under these conditions, the following results are observed:

| Fungicide (a) | Per cent efficacy mg/1 FENPROPIMORPH | | | | | |
|---|---|---|---|---|---|---|
| | 0 | 4 | 12 | 37 | 111 | 333 |
| 0 | 0 | 26.25 | 38.75 | 56.25 | 67.5 | 83.75 |
| 4 | 38.75 | 52.5 | 52.5 | 53.75 | 55 | 67.5 |
| 12 | 61.25 | 52.5 | 52.5 | 52.5 | 75 | 80 |
| 37 | 62.5 | 63.75 | 67.5 | 65 | 71.25 | 90 |
| 111 | 68.75 | 55 | 67.5 | 75 | 86.25 | 92.5 |
| 333 | 75 | 90.75 | 99.5 | 93.75 | 98.5 | 96 |

We claim:

1. A process for the treatment of a plant suffering from, or protection of a plant subject to, fungal diseases which comprises applying to the leaves of the plant a fungicidal and non-phytotoxic amount of a component (a) 2-(4-chlorobenzylidene)-5,5-dimethyl-1-(1H-1,2,4-triazol-1-ylmethyl)-1-cyclopentanol and a component (b) at least one dithiocarbamic acid derivative fungicide, wherein the proportion by weight of component (a) to component (b) is from 0.0003 to 3,000, inclusive.

2. A process for the treatment of a plant suffering from, or protection of a plant subject to, fungal diseases which comprises applying to the leaves of the plant a fungicidal and non-phytotoxic amount of a fungicidal composition comprising a component (a) 2-(4-chlorobenzylidene)-5,5-dimethyl-1-(1H-1,2,4-triazol-1-ylmethyl)-1-cyclopentanol, a component (b) at least one dithiocarbamic acid derivative fungicide and an agriculturally acceptable carrier, wherein the proportion by weight of component (a) to component (b) is from 0.0003 to 3,000, inclusive.

3. The process according to claim 1, wherein the fungal diseases are diseases of cereals, vines, market garden crops, arboricultural crops, tropical crops, rice, maize, beet or rape.

4. The process according to claim 2, wherein the fungal diseases are diseases of cereals, vines, market garden crops, arboricultural crops, tropical crops, rice, maize, beet or rape.

5. The process according to claim 1 wherein
the dithiocarbamic acid derivative is selected from the group consisting of maneb, mancozeb and zineb.

6. The process according to claim 2, wherein
the dithiocarbamic acid derivative is selected from the group consisting of maneb, mancozeb and zineb.

7. The process according to claim 1, wherein the proportion by weight is from 0.001 to 1,000, inclusive.

8. The process according to claim 2, wherein the proportion by weight is from 0.001 to 1,000, inclusive.

9. The process according to claim 1, wherein the amount of component (a) and component (b) applied is 0.002 to 1 kg/ha.

10. The process according to claim 2, wherein the amount of component (a) and component (b) applied is 0.002 to 1 kg/ha.

11. The process according to claim 9, wherein the amount applied is 10 to 600 g/ha.

12. The process according to claim 10, wherein the amount applied is 10 to 600 g/ha.

13. The process according to claim 2 wherein the fungicidal composition further comprises an agriculturally suitable surface-active agent.

14. The process according to claim 5, wherein the dithiocarbamic acid derivative is maneb.

15. The process according to claim 6, wherein the dithiocarbamic acid derivative is maneb.

16. A composition for the protection of a plant suffering from, or subject to, fungal diseases comprising a component (a) 2-(4-chlorobenzylidene)-5,5-dimethyl-1-(1H-1,2,4-triazol-1-ylmethyl)-1-cyclopentanol, a component (b) at least one dithiocarbamic acid derivative fungicide and an agriculturally suitable inert carrier, wherein the proportion by weight of component (a) to component (b) is from 0.0003 to 3,000, inclusive.

17. The composition according to claim 16, wherein the dithiocarbamic acid derivative is selected from the group consisting of maneb, mancozeb and zineb.

18. The composition according to claim 16, wherein the proportion by weight is from 0.001 to 1,000, inclusive.

19. The composition according to claim 17, wherein the dithiocarbamic acid derivative is maneb.

20. The composition according to claim 16 further comprising an agriculturally suitable surface-active agent.

* * * * *